(12) United States Patent
Hallman et al.

(10) Patent No.: US 6,379,040 B1
(45) Date of Patent: Apr. 30, 2002

(54) X-RAY POSITIONING ARM NOISE REDUCTION SYSTEM

(75) Inventors: Darren Lee Hallman, Clifton Park; Philip Alexander Shoemaker, Scotia, both of NY (US); Paul Michael Ratzmann, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/681,961

(22) Filed: Jun. 29, 2001

(51) Int. Cl.[7] ................................ H05G 1/00
(52) U.S. Cl. .............. 378/197; 193/195; 193/196; 193/197; 193/4
(58) Field of Search .............. 378/4, 193, 195, 378/196, 197

(56) References Cited

U.S. PATENT DOCUMENTS 5,503,416 A * 4/1996 Aoki et al. .............. 280/79.11
5,799,054 A * 8/1998 Hum et al. ................ 378/17

* cited by examiner

Primary Examiner—Robert H. Kim
Assistant Examiner—T. Barber
(74) Attorney, Agent, or Firm—McAndrews, Held & Malloy, Ltd.; Peter J. Vogel; Michael A. Dellapenna

(57) ABSTRACT

An x-ray system is provided that produces noise at or below ambient levels. The system includes a positioning arm, an x-ray tube, an x-ray detector, and an acoustic dampening interface mounting between the x-ray tube and a first end of the positioning arm. The acoustic dampening interface may be a rubber isolator that absorbs the vibrations produced by the x-ray tube. The rubber isolator may include a rubber isolation tube positioned within a hole formed in a mounting plate of the x-ray tube. Alternatively, the rubber isolator may include a rubber washer and a rubber isolation layer, or isolation ring.

38 Claims, 7 Drawing Sheets

X-RAY POSITIONING ARM NOISE REDUCTION SYSTEM

BACKGROUND OF THE INVENTION

At least one of the embodiments of the present invention generally relates to improvements in a medical x-ray imaging system, and more particularly relates to an improved interface between a positioning arm and an x-ray tube.

X-ray imaging systems typically include an x-ray tube, a detector, and a positioning arm, such as a C-arm, supporting the x-ray tube and the detector. In operation, an imaging table, on which a patient is positioned, is located between the x-ray tube and the detector. The x-ray tube typically emits radiation, such as X-rays, toward the patient. The radiation typically passes through the patient positioned on the imaging table and impinges on the detector. As the radiation passes through the patient, anatomical structures inside the patient cause spatial variances in the radiation received at the detector. The detector then translates the radiation variances into an image which may be employed for clinical evaluations.

Typically, the x-ray tube is directly mounted to the positioning arm. The x-ray tube is rigidly fastened to the positioning arm through fasteners such as bolts, screws, and the like. Typically, the x-ray tube and the positioning arm directly contact each other through their respective mounting surfaces. Additionally, the x-ray tube and the positioning arm contact each other through the fasteners. That is, one portion of each fastener, such as a head of a bolt, directly contacts the x-ray tube, while the other portion, such as a nut, directly contacts the positioning arm. Washers may be positioned between the mounting surfaces and the fastener. The direct contact between the x-ray tube and positioning arm, and the additional contact from the fasteners typically provide an unimpeded vibrational path between the x-ray tube and the positioning arm.

The x-ray tube typically vibrates during use. The vibrations caused by the x-ray tube may be translated from the x-ray tube to the positioning arm. The subsequent vibration of the positioning arm typically causes acoustic noise. The acoustic noise generated from the vibration of the positioning arm due to the vibration of the x-ray tube may exceed the ambient background noise. The excessive noise generated during x-ray imaging may be unsettling to patients and irritating to physicians and x-ray technicians.

X-rays are produced when high-speed electrons are suddenly decelerated, for example, when a metal target, is struck by electrons that have been accelerated through a potential difference of several thousand volts. Typically, x-ray emitters include an anode and a cathode. In order to manage the resulting heat on the target from the cathode during the x-ray emission process, the anode is rotated at a high rate of speed. Typically, the anode is connected to an axle. The axle is in turn retained by a bearing. The bearing rotates the axle. The bearing is rotated by a motor. Therefore, the rotation of the bearing causes the anode to rotate.

The rotation of the bearing typically causes the x-ray tube to vibrate. That is, the vibrations produced by the bearing are transmitted from the emitter to the x-ray tube casing. The vibrations are then transmitted into the positioning arm, or C-arm through the direct contact of the mounting surfaces of the x-ray tube and the positioning arm. Additionally, the vibrations are also transmitted from the x-ray tube to the fastener. The vibrations are then transmitted from the fastener to the positioning arm. The vibrations translated to the positioning arm produce acoustic noise, or acoustic energy.

The direct-contact interface between the x-ray tube and the positioning arm provides a path along which the vibrations travel. Because the x-ray tube and the positioning arm are securely fastened to one another, the impedance for the transmission of the vibration is matched. The matched impedance provides the vibration an unimpeded path from the x-ray tube to the positioning arm.

In order to diminish the noise produced within x-ray systems, some systems include an expensive fluid film bearing, or spiral groove bearing. The spiral groove bearing uses a liquid metal, such as Gallium, to reduce the vibrations caused by the bearing. Vibration energy in the expensive spiral groove bearing is small due to the fluid film lubrication in the bearing.

Thus a need has existed to reduce the amount of noise produced within x-ray systems. Further a need has existed for an interface that efficiently and inexpensively reduces the amount of noise produced within an x-ray system.

SUMMARY OF THE INVENTION

In accordance with an embodiment of the present invention, an x-ray system has been developed that substantially reduces the amount of acoustic noise produced within the system. The x-ray system includes a positioning arm, such as a C-arm, an x-ray tube, an x-ray detector; and an acoustic dampening interface, or isolation layer. The acoustic dampening interface may be a rubber isolator that mounts between the x-ray tube and a first end, or prong, of the positioning arm. The detector mounts on a second end, or prong, of the positioning arm. The isolator substantially absorbs acoustic energy, in the form of vibrations, generated by the x-ray tube. That is, the isolator causes a vibrational impedance mismatch between the x-ray tube and the positioning arm, or C-arm, when vibrational energy is transmitted from an emitter within the x-ray tube to the rubber isolator.

The x-ray tube includes a vibrational insulation layer. The vibrational insulation includes foam layers separated by a lead barrier layer. The foam layers may be made of polyester foam or urethane foam. In one embodiment of the present invention, the lead barrier layer has a density of one pound per square foot.

The rubber isolator of one embodiment of the present invention includes a rubber isolation tube. The rubber isolation tube extends through a hole formed within a mounting plate of the x-ray tube. The rubber isolation tube clamps onto the tube mounting plate. The rubber isolation tube also includes a steel inner sleeve. The inner sleeve retains a fastener, such as a screw, bolt and the like. The rubber isolation tube isolates, or separates the x-ray tube from direct contact with the fastener.

The rubber isolator of another embodiment of the present invention includes a rubber washer and a rubber isolation ring. The rubber washer isolates, or separates the x-ray tube from direct contact with a fastener. Further, the rubber isolation ring separates the x-ray tube from the positioning arm. In another embodiment, a rubber isolation layer substantially occupies the space between the x-ray tube and the positioning arm.

In another embodiment of the present invention, the noise reduction system may be implemented in a computerized tomography (CT) imaging system. The CT system may include a gantry, a CT tube, and a rubber isolator mounted between the gantry and the CT tube.

BRIEF DESCRIPTION OF DRAWINGS

The foregoing summary, as well as the following detailed description of the preferred embodiments of the present invention, will be better understood when read in conjunction with the appended drawings. For the purpose of illustrating the invention, there is shown in the drawings, embodiments which are present preferred. It should be understood, however, that the present invention is not limited to the precise arrangements and instrumentality shown in the attached drawings.

DETAILED DESCRIPTION

Figure 1:
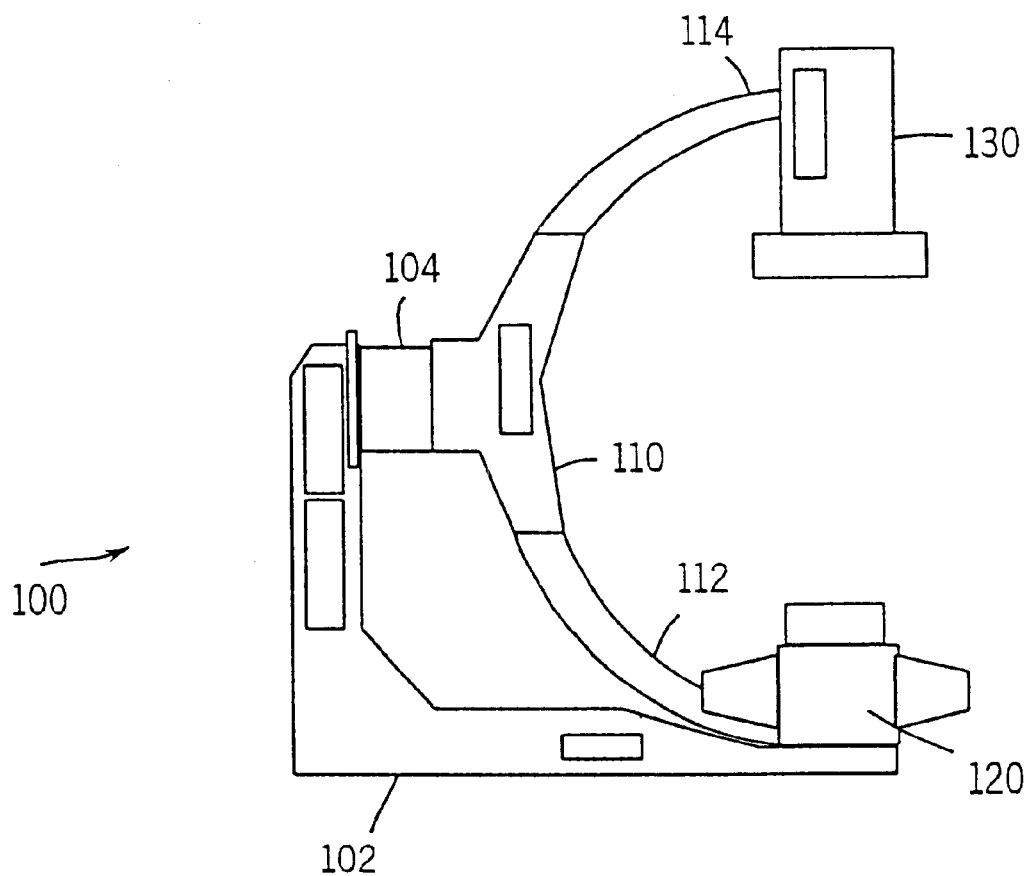
FIG. 1 illustrates an x-ray system formed in accordance with an embodiment of the present invention.

FIG. 1 illustrates an x-ray system 100 formed in accordance with an embodiment of the present invention. The x-ray system 100 includes a base member 102, an intermediate portion 104, a positioning arm 110, such as a C arm, an x-ray tube 120, a detector 130, and an acoustic dampening interface (shown below with respect to FIGS. 3 and 4). The positioning arm 110 includes a first end, or first prong 112, and a second end, or second prong 114.

The base member 102 supports the entire structure of the x-ray system 100. The base member 102 is connected to the intermediate portion 104, which is in turn connected to the positioning arm, or C-arm 110. The first extension, or first prong 112 connects to the x-ray tube 120 through the acoustic dampening interface. The second extension, or second prong 114 connects to the detector 130. The x-ray tube 120 and the detector 130 are oriented such that the x-ray tube 120 emits radiation toward the detector 130.

In operation, a patient is positioned on an x-ray positioning table (not shown) between the x-ray tube 120 and the x-ray detector 130. After the patient is positioned, the imaging process may begin. To begin the imaging process the imaging tube 120 is activated. During imaging, the x-ray tube 120 emits radiation that passes through the patient and is received by the detector 130.

Figure 2:
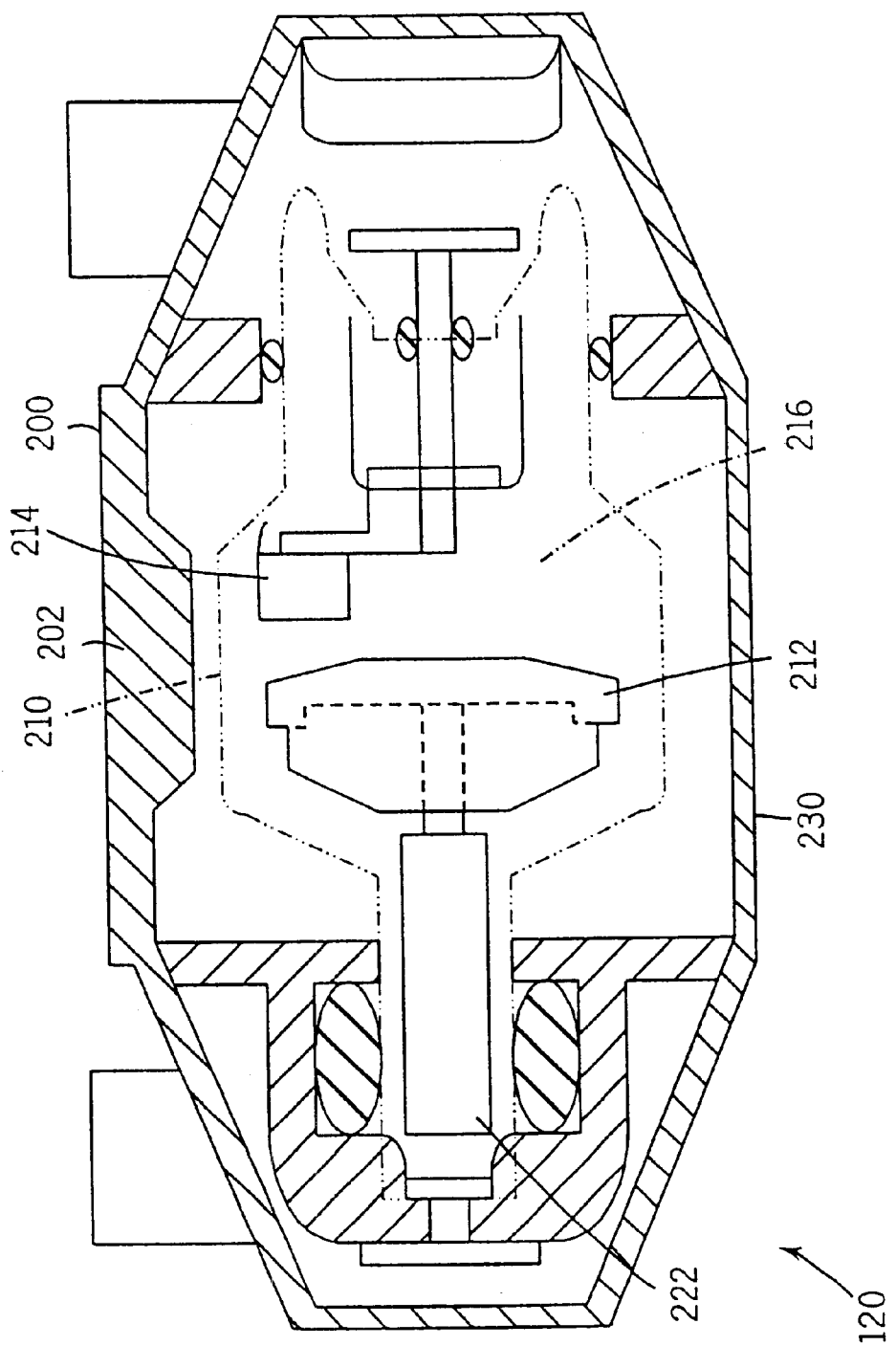
FIG. 2 illustrates an x-ray tube formed in accordance with an embodiment of the present invention.

FIG. 2 illustrates an x-ray tube 120 formed in accordance with an embodiment of the present invention. The x-ray tube 120 includes a casing 200, a radiation emission passage 202 formed within the casing and a mounting plate 230 on the side of the x-ray tube 120 opposite that of the emission passage 202. The casing 200 encloses an insert, or emitter 210, which houses the internal components of the x-ray tube 120. The internal components include an anode 212, an extension rod 222, such as an axle and a cathode 214, and a bearing (not shown) within a vacuum 216. The cathode 214 and anode 212 are mounted within the interior of the insert 210. The anode 212 connects to the extension rod 222. The opposite end of the extension rod 222 is retained by the bearing. The bearing is in turn retained by an additional structure, such as a motor mounted within the insert 210.

The insert 210 is in turn mounted within the casing 200. As further described below with respect to FIG. 7, the x-ray tube 120 is insulated with a vibrational insulation layer (not shown with respect to FIG. 2) that includes foam layers and a barrier layer. The vibrational insulation layer is affixed to the interior of the casing 200.

As mentioned above, x-rays are produced when high-speed electrons are suddenly decelerated, for example, when a metal target, that is the anode 212, is struck by electrons that have been accelerated through a potential difference of more than 80 thousand volts. The x-rays are then emitted through the radiation emission passage 202 toward the detector 130. In order to manage the resulting heat on the anode 212 from the cathode 214, the anode 212 is rotated at a high rate of speed. As stated above, the anode 212 is connected to the axle 222. The axle 222 is rotated through the bearing, which is activated by the motor. The rotation of the bearing 220 causes the axle 222 to rotate. The rotation of the axle 222 causes the anode 212 to rotate. The bearing 220 rotates the anode 212 at a high rate, for example 125 Hz. The high rate of rotation of the bearing and the anode 212 causes the insert 210 to vibrate. The vibration of the insert 210 in turn causes the casing 200 to vibrate. The vibrations are transmitted from the insert 210 into the casing 200. However, the vibrations are not substantially transmitted into the positioning arm 110. Rather, the rubber isolator, or isolator layer substantially absorbs the vibrations, and therefore substantially reduces the amount of sound energy, or acoustic noise produced within the positioning arm 110 by the transmitted vibrations. That is, the isolation layer substantially impedes the progress of vibrations, or sound energy into the positioning arm 110.

Figure 7:
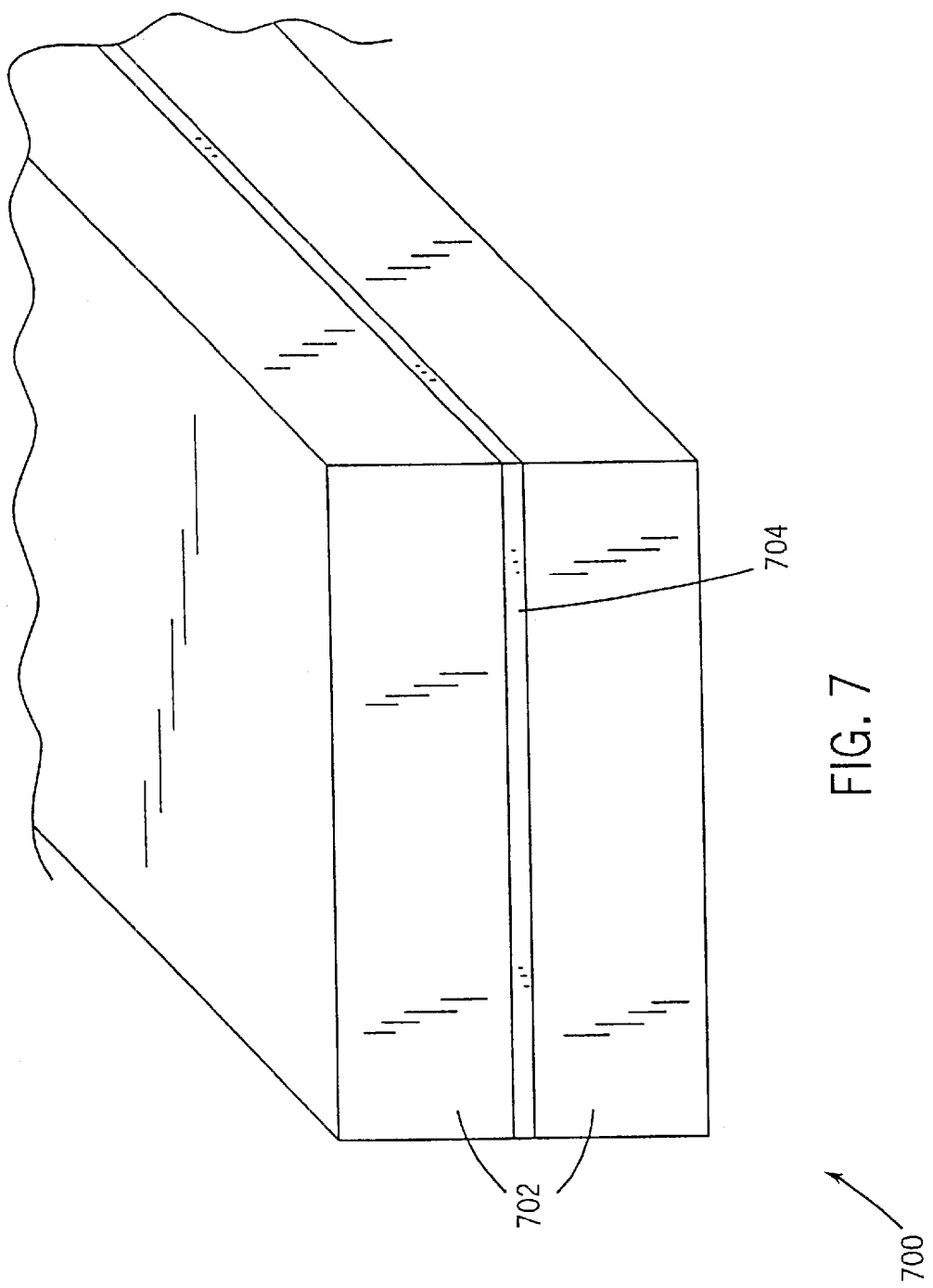
FIG. 7 illustrates a vibrational insulation layer of an x-ray tube formed in accordance with an embodiment of the present invention.

FIG. 7 illustrates the vibrational insulation layer 700 of the x-ray tube 120 formed in accordance with an embodiment of the present invention. The vibrational insulation layer 700 includes foam layers 702 and a barrier layer 704. The foam insulation layers 702 may be made of polyester or urethane foam. The barrier layer 704 is made of lead or another high density material. The barrier layer 704 is fastened between the foam layers 702 through a fastening agent, such as glue.

The vibrational insulation layer 700 is fastened to the interior of the casing 200 through an adhesive material such as glue. The vibrational insulation layer 700 conforms to the contours of the interior of the casing 200. Each foam layer 702 is approximately one inch thick. Alternatively, each foam layer 702 may be more or less than one inch thick. The density of the barrier layer 704 is approximately one pound per square foot. Alternatively, the density of the barrier layer 704 may be more or less than one pound per square foot.

Figure 3:
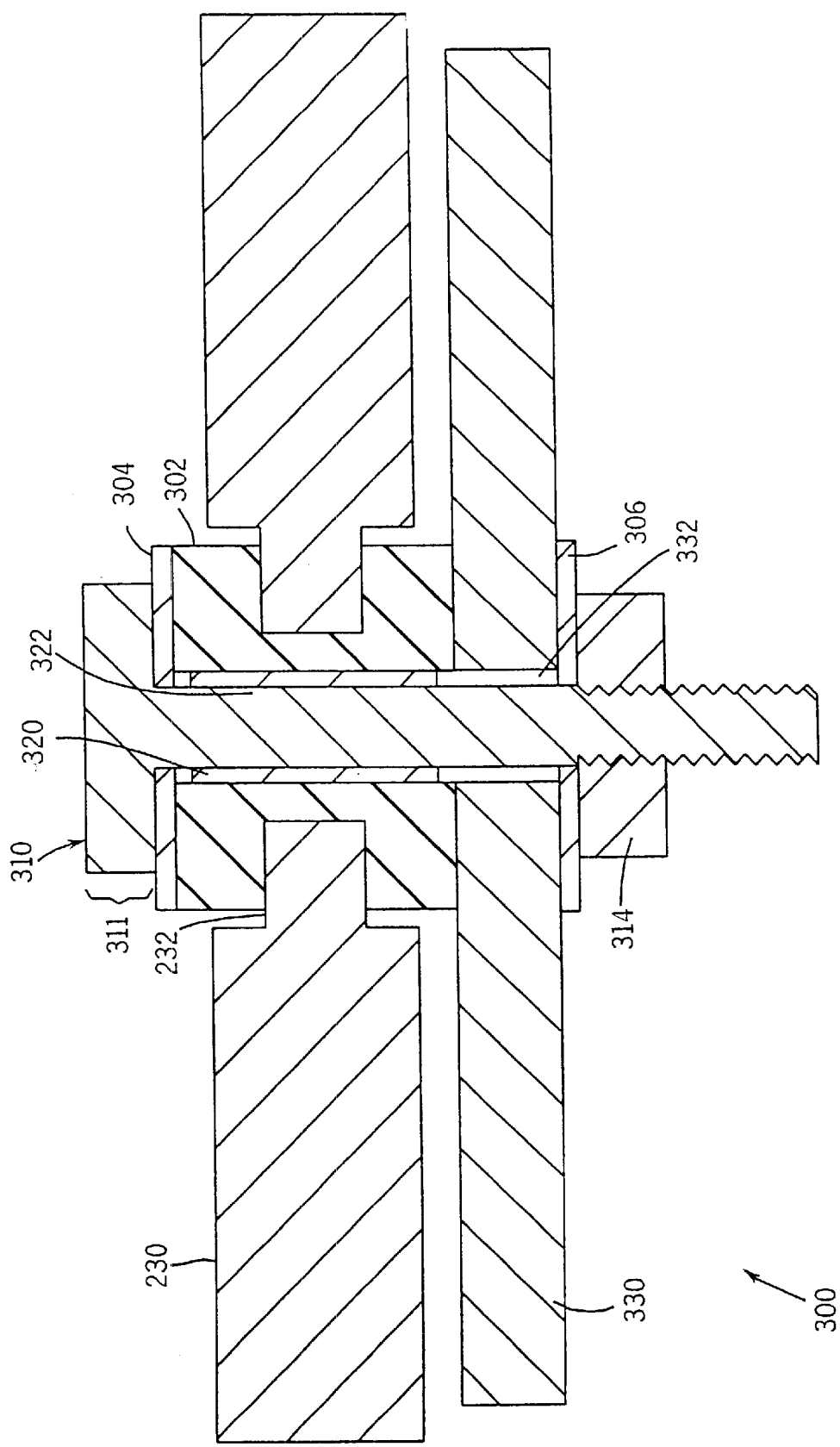
FIG. 3 illustrates a transverse cross-sectional view of a point isolation interface formed in accordance with an embodiment of the present invention.

FIG. 3 illustrates a transverse cross-sectional view of a point isolation layer interface 300 formed in accordance with an embodiment of the present invention. The interface 300 includes the mounting plate 230 of the x-ray tube 120, a rubber isolation tube 302, washers 304, 306, a fastener, such as a screw 310 including a head 311, a nut 314, a steel inner sleeve 320 defining a fastener passage 322, and an arm mounting plate 330. The mounting plate 230 includes a reduced portion 232 surrounding a hole (occupied by the rubber isolation tube 302) formed in the mounting plate 230. A hole 332 is also formed in the arm mounting plate 330.

The rubber isolation tube 302 is positioned within the hole formed in the mounting plate 330. As shown in FIG. 3, the rubber isolation tube 302 is rigidly fastened to the mounting plate 230. The rubber isolation tube 302 clamps down onto the reduced portion 232 of the mounting plate 230.

Optionally, the rubber isolation tube 302 may be fastened to the reduced portion 232 by an additional fastening agent, such as glue. The rubber isolation tube 302 includes a steel inner sleeve 320. The exterior surface of the steel inner sleeve 320 is bonded, or fastened to the interior surface of the rubber isolation tube 320. The inner sleeve 320 may be grooved in order to allow passage of the screw 310.

The x-ray tube 120 and the positioning arm 110 do not directly contact one another. Rather, the mounting plate 230 is positioned on top of the arm mounting plate 330 such that the bottom portion of the rubber isolation tube 302 is positioned between the mounting plate 230 and the arm mounting plate 330. The mounting plate 230 and the arm mounting plate 330 are separated by the rubber isolation tube 302. The rubber isolation tube 302 is positioned such that the fastener passage 322 and the hole 332 formed in the arm mounting plate 330 are aligned with each other. The fastener 310 does not directly contact the mounting plate 230. The fastener 310, such as a screw, is retained by the inner sleeve 320. Therefore, the mounting plate 230 is separated from the fastener 310 by the rubber isolation tube 302 and the inner sleeve 320. The washer 304 is positioned between the head 311 of the fastener 310 and the top surface of the rubber isolation tube 302.

The fastener 310 is long enough to pass through the inner sleeve 320 and the hole 332 formed in the arm mounting plate 330. The nut 314 is threaded on the fastener 310. The washer 306 separates the nut 314 from the arm mounting plate 330. Thus, the mounting plate 230 of the x-ray tube 120 may be securely fastened to the arm mounting surface 330 of the positioning arm 110 with the rubber isolation tube 302 separating the mounting plate 230 of the x-ray tube 120 from the arm mounting plate 330 of the positioning arm 110. Additional point isolation interfaces 300 may be positioned between the mounting plate 230 of the x-ray tube 120 and the arm mounting plate 330. For example, three point isolation interfaces 300 may be utilized to provide added support.

As a vibration travels from the x-ray tube 120 into the rubber isolation tube 302, an impedance mismatch occurs between the rubber isolation tube 302 and the x-ray tube 120. Even though the fastener 310 securely fastens the x-ray tube 120 to the positioning arm 110 through the rubber isolation tube 302, the transmission of the vibration, or vibratory sound wave, is absorbed by the rubber isolation tube 302. Because no part of the x-ray tube 120 directly contacts the fastener 311 or the positioning arm 110, vibrations generated within the x-ray emitter, or insert 210 are substantially absorbed by the rubber isolation tube 302 and not transmitted to the positioning arm 110.

Figure 4:
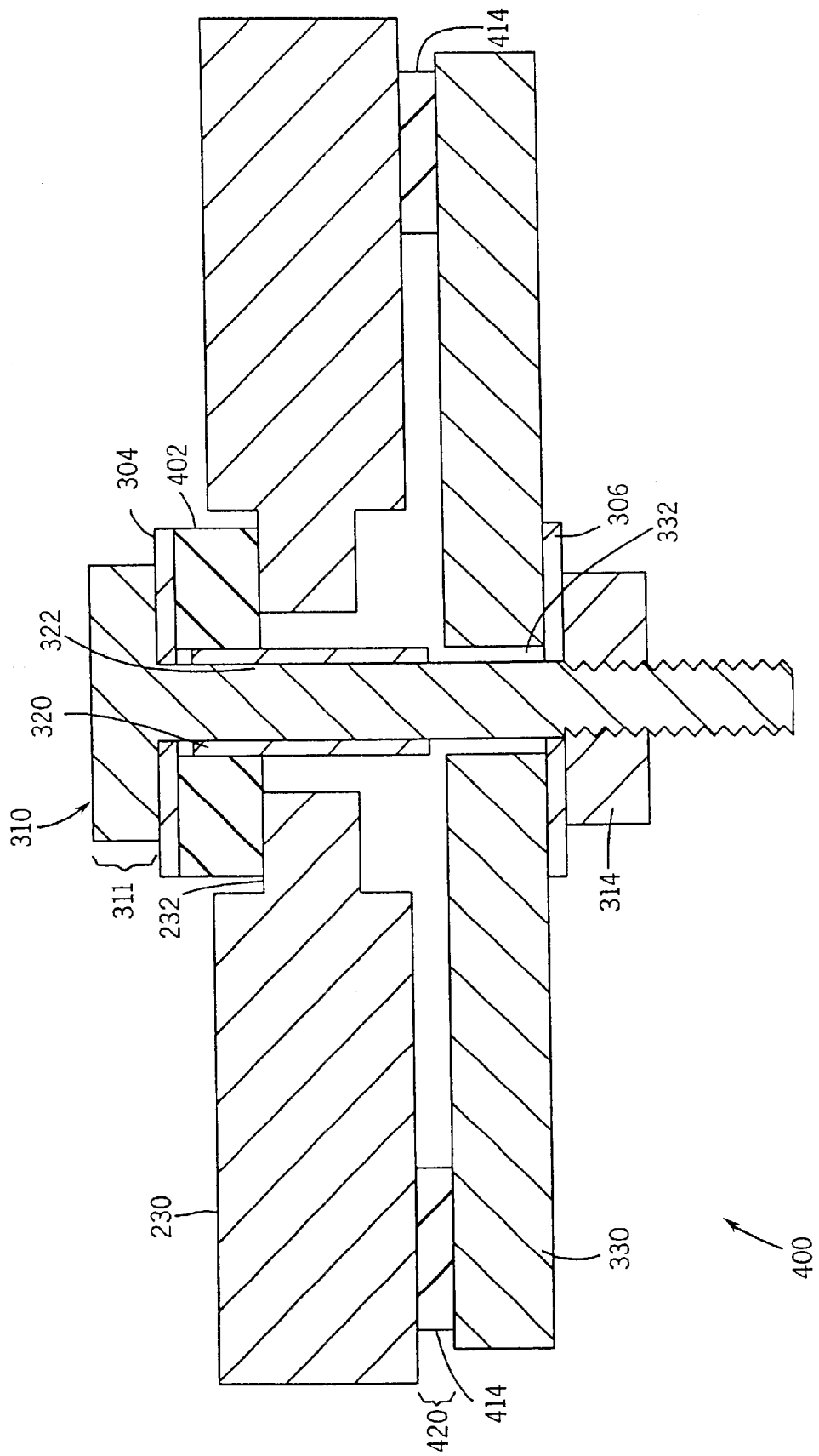
FIG. 4 illustrates a transverse cross-sectional view of a plate isolation interface formed in accordance with an embodiment of the present invention.

FIG. 4 illustrates a transverse cross-sectional view of a plate isolation interface 400 formed in accordance with an embodiment of the present invention. Instead of using a rubber isolation tube 302, as shown in FIG. 3, a rubber isolating washer 402 and a rubber isolation ring 414 are used. The sleeve 320 extends downward from the rubber washer 402. The rubber washer 402 is positioned on top of the reduced portion of the mounting plate 230 (as opposed to clamping onto the mounting plate 230 as the rubber isolation tube 302 of FIG. 3). The rubber washer 402 is held into position by the fastener 310. The rubber washer 402 may also be bonded or fastened (by a fastening agent such as glue) to the reduced portion 232 of the mounting plate 230. The rubber isolation ring 230 separates the mounting plate 230 from the positioning arm plate 330. In another embodiment, a rubber isolation layer between the x-ray tube 120 and the positioning arm 110 may substantially occupy the space 420 between the x-ray tube 120 and the positioning arm 110. That is, the rubber isolation layer may fill the space 420, except the space occupied by the fastening agent 310 and the inner sleeve 320, between the x-ray tube 120 and the positioning arm 110.

No part of the mounting plate 230, and therefore the x-ray tube 120, directly contacts the arm mounting plate 330, and therefore the positioning arm 110. Further, the fastener 310 does not directly contact the mounting plate 230. Thus, while the x-ray tube 120 and the positioning arm 110 are securely fastened to each other, they are separated from each other by the rubber isolation ring 414. Neither the fastener 310, nor the positioning arm 110 directly contacts the x-ray tube 120. Consequently, any vibratory transmission produced within the x-ray tube 120 is substantially absorbed by the rubber isolating washer 402 and the rubber isolation ring 414.

Figure 6:
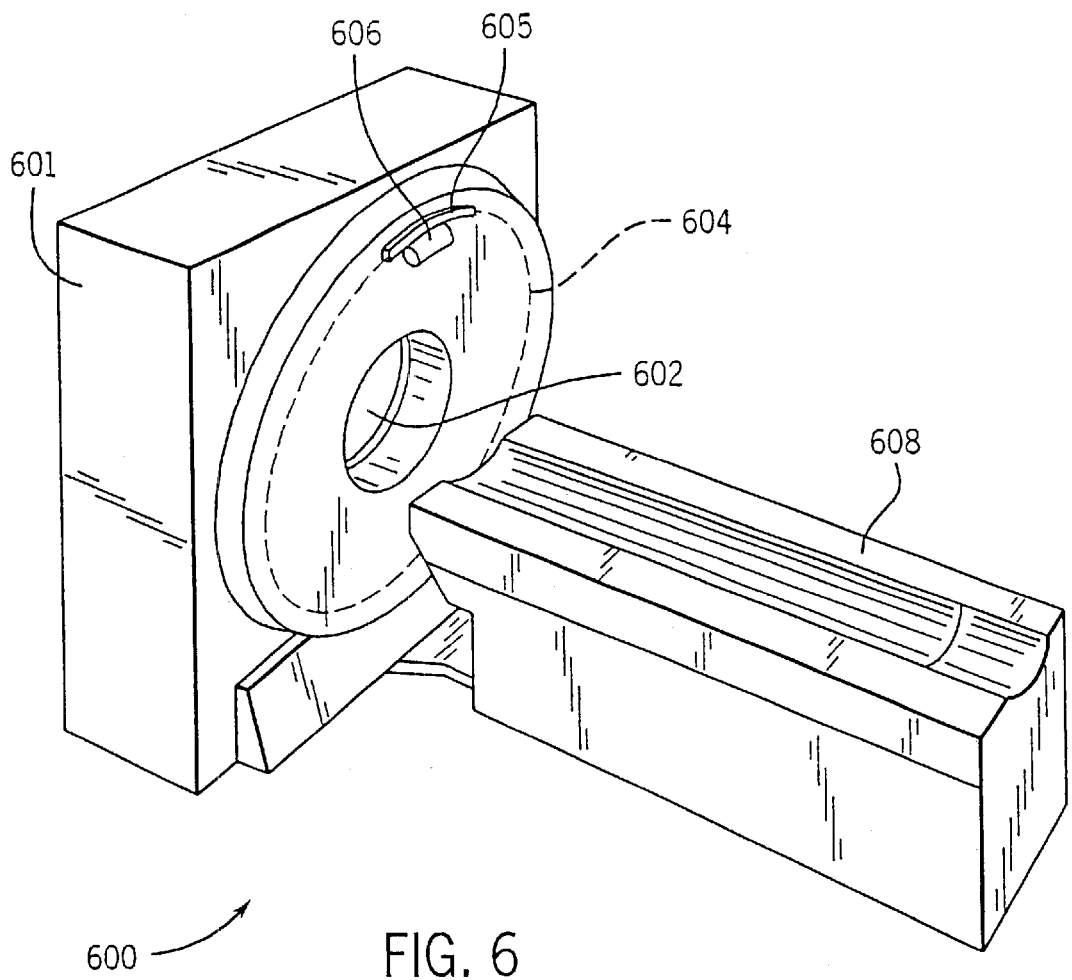
FIG. 6 illustrates a computerized tomography system formed in accordance with the present invention.

In accordance with an alternative embodiment, the acoustic dampening interfaces shown in FIGS. 3 and 4 may also be used with computerized tomography (CT) systems. FIG. 6 illustrates a computerized tomography 600 system formed in accordance with the present invention. The CT system 600 includes a positioning table 608 and an imaging unit 601. The imaging unit 601 includes a patient positioning chamber 602, a CT tube 606, and a movable gantry 605 attached to a track 604. The CT tube 606, the movable gantry 605 and the track 604 are contained within the imaging unit 601. The CT tube 606 is attached to the gantry 605. Therefore, the CT tube 606 may be rotated around the positioning chamber 602 by way of the gantry 605. The CT tube 606 may be fastened to the gantry 605 through a rubber isolation layer in the same way as the x-ray tube 120 is fastened to the positioning arm 110. That is, the CT 606 is fastened to the gantry 605 by way of an acoustic dampening interface, such as the rubber isolation tube 302 of FIG. 3 or the rubber isolation ring 414 of FIG. 4. In operation, a patient is placed within the patient positioning chamber 602. The gantry 605 moves the CT tube 606 around the patient positioning chamber 602. The gantry 605, and therefore the CT tube 606, may be rotated 360 degrees around the positioning chamber 602. The CT tube 606 is securely fastened to a gantry mounting plate (not shown) in a similar fashion as the CT tube 120 is securely fastened to the positioning arm 110, as shown in FIGS. 3 and 4.

Figure 5:
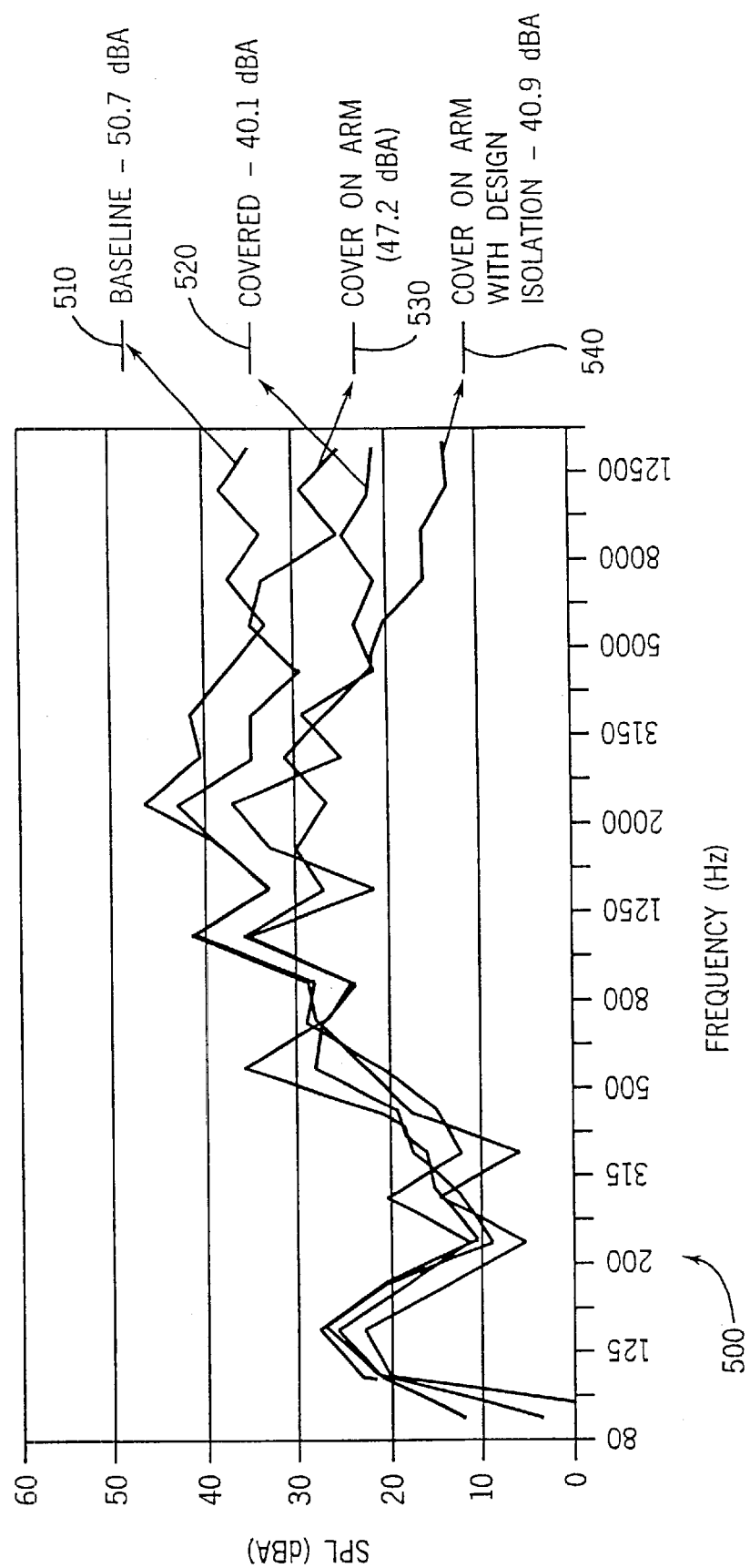
FIG. 5 is a sound presence level chart according to an embodiment of the present invention.

FIG. 5 is a sound presence level chart 500 according to an embodiment of the present invention. The chart 500 compares sound presence levels of: an x-ray tube that is not mounted, nor covered at baseline 510; an x-ray tube that is covered, but not mounted at line 520; a mounted, covered x-ray tube at line 530; and an x-ray tube according to an embodiment of the present invention, that is, an x-ray tube that is covered and mounted with a rubber isolation layer, as shown in FIGS. 3 or 4, at line 540. The sound presence level is measured in dBA. The unit dBA represents an A-weighted dB. A-weighting is a frequency dependence that mimics what the human ear hears. For example, acoustic or sound energy, that is, noise, has a total sound pressure over multiple frequency bands. A-weighting represents what the human ear hears. The human ear does not hear all frequencies the same. Rather, the human ear is sensitive to different frequency bands. The human ear typically hears high frequencies better than low frequencies. A-weighting is a system that takes into account the degree to which the human ear hears various frequency ranges.

As shown in FIG. 5, a sound pressure level of 50.7 dBA was measured for an uncovered x-ray tube and represented on the chart 500 by baseline 510. The sound pressure level of the covered, unmounted x-ray tube was measured at 40.1 dBA and represented on the chart 500 by line 520. When the covered x-ray tube was mounted on the C-arm, or positioning arm without a rubber isolation layer between the x-ray tube and the positioning arm, a sound pressure level of 47.2 dBA was measured, and represented on the chart 500 by line 530. The 7.1 dBA difference between line 530 and line 520 resulted from the transmission of vibratory sound energy into the positioning arm, or C-arm. However, the mounted covered x-ray tube with the rubber isolation layer produced a sound pressure level of 40.9 dBA. The difference between line 540 and line 520 is 0.8 dBA. Therefore, the rubber isolation layer, or rubber isolator, substantially absorbed the amount of vibratory sound energy produced by the x-ray tube.

Thus at least one embodiment of the present invention reduces the amount of noise produced within x-ray systems. Further, at least one embodiment of the present invention efficiently and inexpensively reduces the amount of noise produced within an x-ray system.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications that incorporate those features coming within the scope of the invention.

What is claimed is:

1. An x-ray system including:
   an x-ray tube;
   an x-ray detector;
   a positioning arm having a first end supporting said x-ray tube and a second end supporting said detector; and
   an acoustic dampening interface mounting between said x-ray tube and said first end of said positioning arm for isolating acoustic waves generated in said x-ray tube from said positioning arm.

2. The system of claim 1 wherein said acoustic dampening interface includes a rubber isolation tube that extends through a hole formed within a mounting plate of said x-ray tube.

3. The system of claim 2 wherein said rubber isolation tube includes an inner sleeve, wherein said inner sleeve retains a fastener, and wherein said rubber isolation tube isolates said x-ray tube from direct contact with said fastener.

4. The system of claim 3 wherein said inner sleeve is composed of steel.

5. The system of claim 1 wherein said acoustic dampening interface includes a rubber washer and a rubber isolation ring, wherein said rubber washer isolates said x-ray tube from direct contact with a fastener, and wherein said rubber isolation ring separates said x-ray tube from said positioning arm.

6. The system of claim 1 wherein said acoustic dampening interface substantially absorbs acoustic energy generated by said x-ray tube.

7. The system of claim 1 further including a patient positioning table located between said x-ray tube and said x-ray detector.

8. The system of claim 1 wherein said x-ray tube includes an insulation layer, and wherein said insulation layer includes a foam layer and a barrier layer.

9. The system of claim 8 wherein said foam layer is a polyester foam layer.

10. The system of claim 8 wherein said foam layer is a urethane foam layer.

11. The system of claim 8 wherein said barrier layer is a lead barrier layer.

12. The system of claim 8 wherein said barrier layer has a density of one pound per square foot.

13. A system for reducing the amount of acoustic noise produced within an x-ray system including:
    a C-arm having a first prong;
    an x-ray tube affixed to a mounting plate that is affixed to said C-arm; and
    an acoustic isolation tube positioned within a hole formed within said mounting plate, said isolation tube clamping to said mounting plate, said isolation tube extending through said hole formed within said mounting plate, and said isolation tube separating said first prong of said C-arm from said x-ray tube.

14. The system of claim 13 wherein said isolation tube includes an inner sleeve, wherein said inner sleeve retains a fastener, and wherein said isolation tube isolates said x-ray tube from direct contact with said fastener.

15. The system of claim 14 wherein said inner sleeve is composed of steel.

16. The system of claim 13 wherein said isolation tube causes an acoustical impedance mismatch between said x-ray tube and said C-arm when sound waves are transmitted from an emitter within said x-ray tube to said rubber isolation tube.

17. The system of claim 13 wherein said x-ray tube includes a vibrational insulation layer, and wherein said vibrational insulation layer includes two foam layers and a barrier layer separating said foam layers.

18. The system of claim 17 wherein said foam layers are polyester foam layers.

19. The system of claim 17 wherein said foam layers are urethane foam layers.

20. The system of claim 17 wherein said barrier layer is a lead barrier layer.

21. The system of claim 17 wherein said barrier layer has a density of one pound per square foot.

22. A system for reducing the amount of acoustic noise produced within an x-ray system including:
    a C-arm having a first prong;
    an x-ray tube securely fastening through a fastener to said first prong of said C-arm;
    a rubber washer isolating said x-ray tube from direct contact with said fastener; and
    a rubber isolation layer separating said x-ray tube from said first prong of said C-arm.

23. The system of claim 22 wherein said rubber washer and said rubber isolation ring substantially absorb vibrations generated by said x-ray tube.

24. The system of claim 22 wherein said rubber isolation layer is a rubber isolation ring.

25. The system of claim 22 wherein said rubber isolation layer substantially occupies the space between said x-ray tube and said first prong of said C-arm.

26. The system of claim 22 wherein said x-ray tube includes a vibrational insulation layer, and wherein said vibrational insulation layer includes a foam layer and a barrier layer.

27. The system of claim 26 wherein said foam layer is at least one of a polyester foam layer and a urethane foam layer.

28. The system of claim 26 wherein said barrier layer is a lead barrier layer.

29. The system of claim 26 wherein said barrier layer has a density of one pound per square foot.

30. A system for reducing the level of noise produced within a computerized tomography (CT) imaging system including:
   a gantry;
   a CT tube supported by said gantry; and
   a rubber isolator mounted between said gantry and said CT tube.

31. The system of claim 30 wherein said isolator includes a rubber isolation tube, and wherein said rubber isolation tube extends through a hole formed within a mounting plate of said CT tube.

32. The system of claim 31 wherein said rubber isolation tube includes an inner sleeve, wherein said inner sleeve retains a fastener, and wherein said rubber isolation tube isolates said x-ray tube from direct contact with said fastener.

33. The system of claim 32 wherein said inner sleeve is composed of steel.

34. The system of claim 30 wherein said isolator includes a rubber washer and a rubber isolation ring, wherein said rubber washer isolates said x-ray tube from direct contact with a fastener, and wherein said rubber isolation ring separates said x-ray tube from said positioning arm.

35. The system of claim 30 wherein said isolator substantially absorbs acoustic energy generated by said x-ray tube.

36. The system of claim 30 wherein said CT tube includes a vibrational insulation layer, and wherein said vibrational insulation layer includes a foam insulation layer and a barrier layer.

37. The system of claim 36 wherein said foam layer is at least one of a polyester foam layer and a urethane foam layer.

38. The system of claim 36 wherein said barrier layer is a lead barrier layer, and wherein said lead barrier layer has a density of one pound per square foot.

* * * * *